US00PP27444P3

(12) United States Plant Patent
Liao

(10) Patent No.: US PP27,444 P3
(45) Date of Patent: Dec. 6, 2016

(54) ***PHALAENOPSIS* PLANT NAMED 'TJ PURPLE QUEEN'**

(50) Latin Name: ***Phalaenopsis* hybrid**
Varietal Denomination: TJ Purple Queen

(71) Applicant: Chang-Lian Lin, San Jose, CA (US)

(72) Inventor: Yuan-Yang Liao, Tainan (TW)

(73) Assignee: Chang-Lian Lin, San Jose, CA (US)

( * ) Notice: Subject to any disclaimer, the term of this patent is extended or adjusted under 35 U.S.C. 154(b) by 74 days.

(21) Appl. No.: 14/121,698

(22) Filed: Oct. 8, 2014

(65) Prior Publication Data

US 2016/0106017 P1 Apr. 14, 2016

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — June Hwu
(74) *Attorney, Agent, or Firm* — Muncy, Geissler, Olds & Lowe, P.C.

(57) ABSTRACT

A new and distinct cultivar named 'TJ PURPLE QUEEN' is disclosed, characterized by unique flowers which are large white with dark pink violet petals and compact plant habit. The new variety is a *Phalaenopsis* hybrid cultivar, and is normally used as an ornamental plant with long and sturdy inflorescences.

4 Drawing Sheets

FIELD OF THE INVENTION

Botanical classification: *Phalaenopsis* hybrid.
Variety denomination: 'TJ Purple Queen'.

BACKGROUND OF THE INVENTION

The present invention comprises a new and distinct *Phalaenopsis* hybrid Orchid cultivar, and hereinafter referred to by the cultivar name, 'TJ Purple Queen'.

The new cultivar was discovered as part of a commercial breeding program, carried out in a commercial greenhouse in Tainan, Taiwan. The inventor, Yuan Yang Liao, a citizen of Taiwan, discovered the new variety as the result of the crossing of the female parent, the unpatented variety *Phalaenopsis* hybrid 'Sogo Yukidian' (not patented) with the male parent, the unpatented variety *Phalaenopsis* hybrid 'I-Hsin Spotted Deer' (not patented). The crossing was performed in April 2006. The new variety was discovered in March 2006 by the inventor.

Asexual reproduction of the new cultivar 'TJ Purple Queen' by stem propagation and meristem tissue culture was performed at a commercial laboratory in Tainan, Taiwan later in 2006. Since that time, many generations have been reproduced, and have shown that the unique features of this cultivar are stable and reproduced true to type through successive generations.

SUMMARY OF THE INVENTION

In the following description, color references are made to The Royal Horticultural Society Mini Colour Chart (R.H.S. color chart), 2005 edition, except where general terms of ordinary dictionary significance are used.

The cultivar 'TJ Purple Queen' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TJ Purple Queen'. These characteristics in combination distinguish 'TJ Purple Queen' as a new and distinct *Phalaenopsis* hybrid cultivar:

1. This plant has shorter and folding upright leaves compared to those of the other plant with similar size of flowers.
2. Unique pure and clear white with real purple bloom coloration.
3. Velvety sepal and petal texture.
4. PARENT COMPARISON:

Plants of the new cultivar 'TJ Purple Queen' are similar to plants of the seed parent variety *Phalaenopsis* hybrid 'Sogo Yukidian' (not patented) in some horticultural characteristics. However, plants of the new cultivar 'TJ Purple Queen' inherited the rough sepals and petals from this seed parent. Additionally, plants of 'TJ Purple Queen' produce white flowers (RHS N999D) with dark pink violet spots (RHS N81B), whereas 'Sogo Yukidian' has only the big white flowers (RHS 155C). Plants of the new cultivar 'TJ Purple Queen' are more similar to plants of the pollen parent variety, *Phalaenopsis* hybrid 'I-Hsin Spotted Deer' (not patented) in most horticultural characteristics. However, plants of the new cultivar 'TJ Purple Queen' produce white flowers with ink-like purple spots, whereas 'I-Hsin Spotted Deer' produces white (RHS N999D) colored flowers with red-purple brown spots (RHS 59B).

BRIEF DESCRIPTION OF THE DRAWINGS

Colors in the photographs may appear different from the color values that appear in the detailed botanical description which more accurately describe the new cultivar.

The photograph was taken using conventional techniques and although colors may appear different from actual colors due to light reflectance it is as accurate as possible by conventional photographic techniques.

DETAILED DESCRIPTION OF THE PREFERRED EMBODIMENTS

Figure 1:
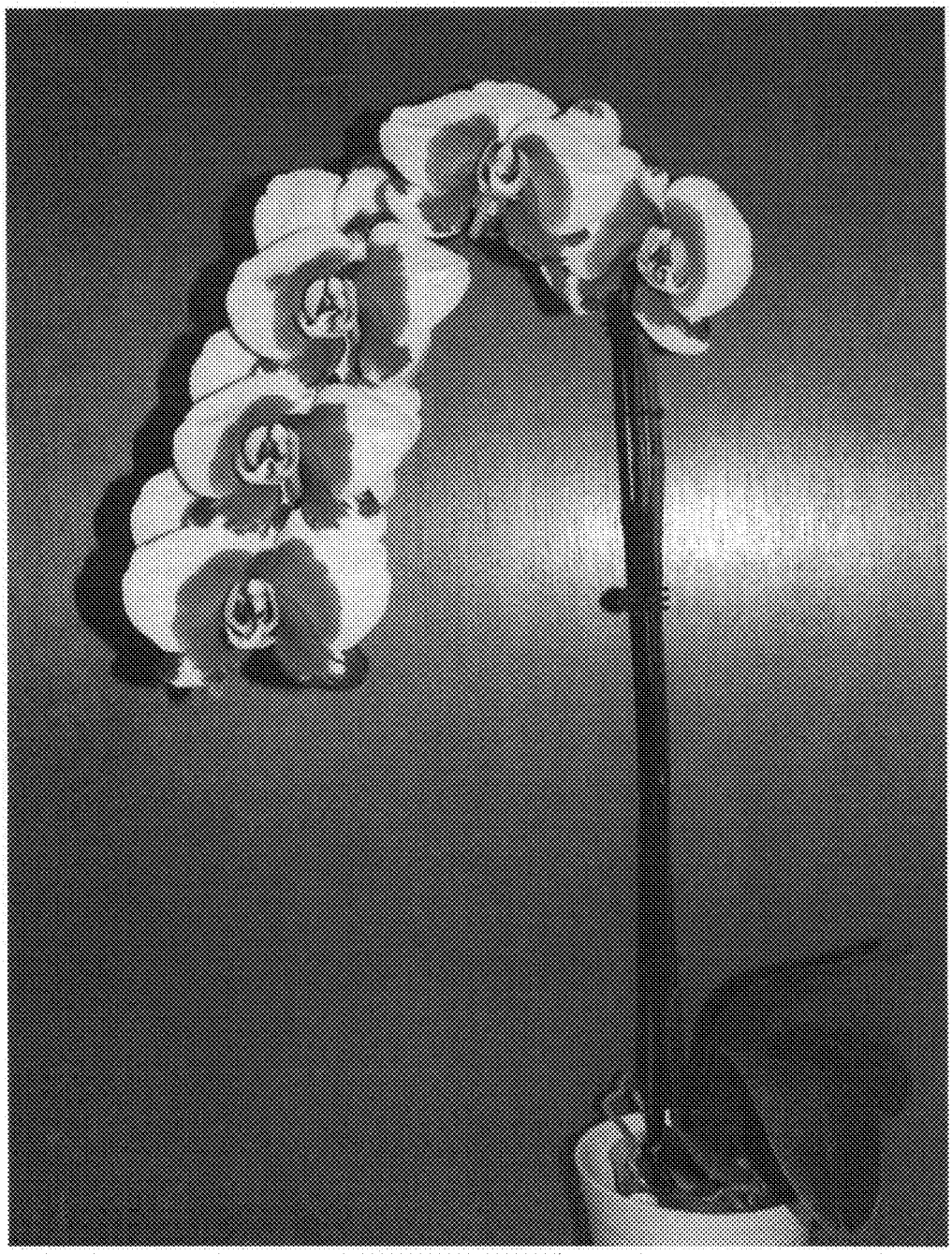
FIG. 1 is a side view of a plant of 'TJ Purple Queen' flowering in the commercial 9 cm pot.
Figure 2:
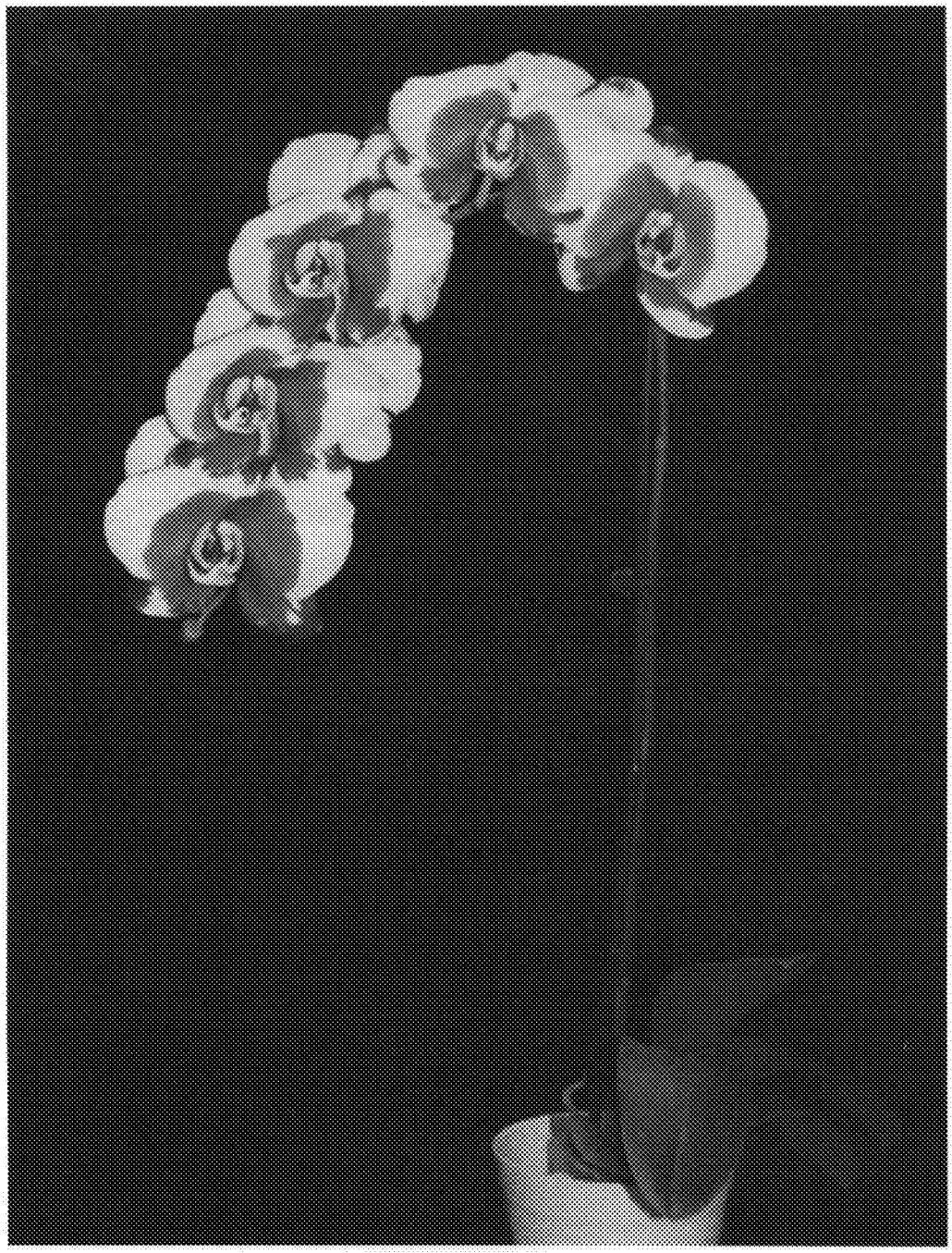
FIG. 2 is a side view of a plant of 'TJ Purple Queen' flowering in the commercial 9 cm pot with all black background.
Figure 3:
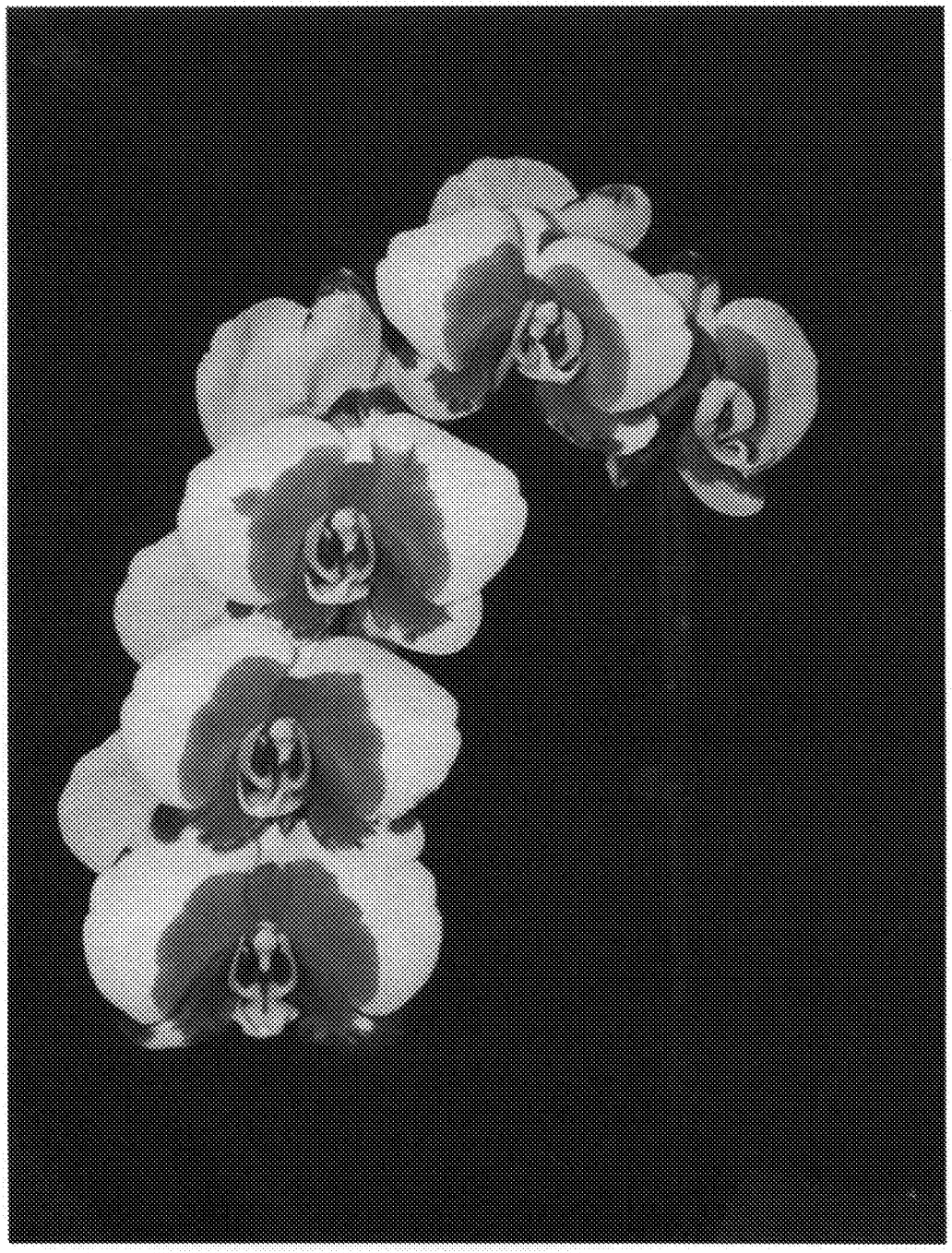
FIG. 3 is a side view of a plant of 'TJ Purple Queen' showing the characteristics of the flowers.
Figure 4:
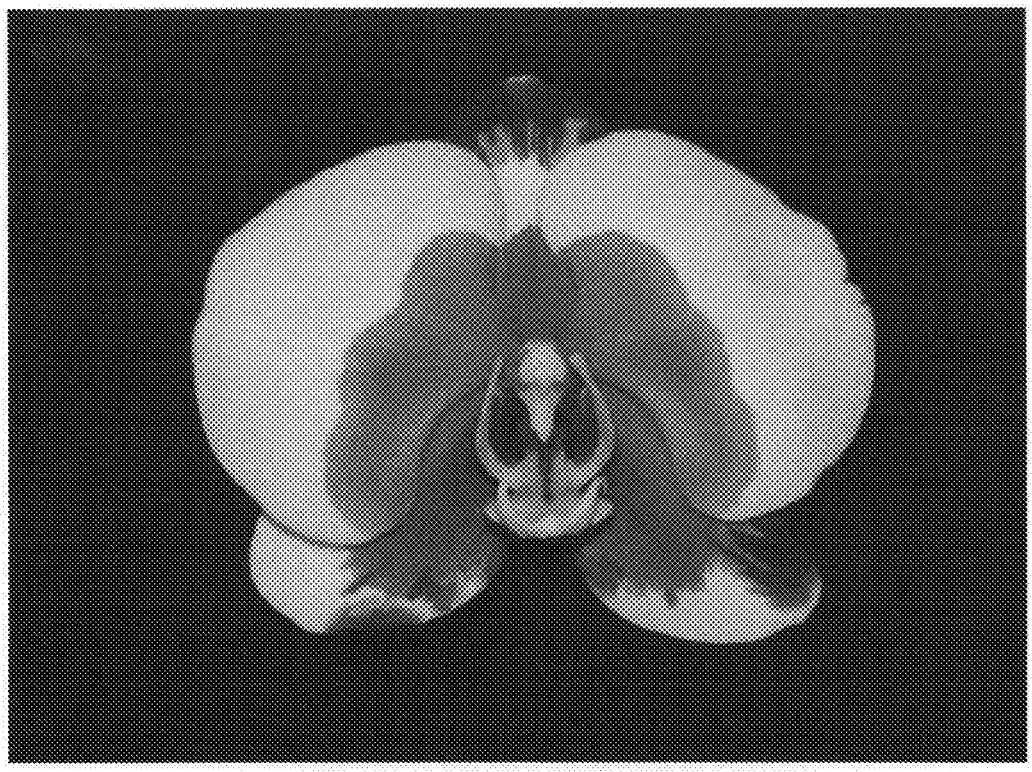
FIG. 4 is a close-up view showing the characteristics of the flower.

The following observations and measurements describe 'TJ Purple Queen' plants grown in a commercial greenhouse in Tainan, Taiwan. Temperature ranged from 23° C. to 26° C. day and from 16° C. to 20° C. night. Light levels ranged from 10,000 lux as a young plant to approximately 20,000 lux for a flowering plant. Plants described began flowering in the end of winter. Measurements and numerical values represent averages of typical flowering types. No chemical or photoperiodic treatments were given.

Parentage:

*Seed.*—*Phalaenopsis* hybrid 'Sogo Yukidian' (not patented).

*Pollen.*—*Phalaenopsis* hybrid 'I-Hsin Spotted Deer' (not patented).

Propagation:

*Type of propagation typically used.*—Tissue culture.

*Time to initiate roots.*—About 40 days at approximately 28-32° C.

*Time to produce a rooted cutting/liner.*—About 5-6 months after cloning at approximately 28-35° C.

*Root description.*—Thick (typical for Phalaenopsis) and rounded, average diameter 5 mm, colored near RHS Yellow Green 145A.

Plant description:

*Plant shape.*—Two-ranked leaves affixed to a short central stem (monopodial growth). Single flowers arranged on upright and sturdy flowering racemes.

*Plant height, soil level to top of foliar plane.*—About 20 to 25 cm.

*Plant height, soil level to top of inflorescences.*—About 55 to 65 cm.

*Plant diameter.*—About 25 to 35 cm.

Flowers per stem: Approximately 8 to 10.

Foliage description:

*Leaf arrangement.*—Distichous.

*Quantity per plant.*—About 6 to 7.

*Length.*—About 20 to 25 cm.

*Width.*—About 6 to 7 cm.

*Shape.*—Obovate.

*Apex.*—Unequal acute.

*Base.*—Cuneate

*Sheath length.*—Average 2.1 cm.

*Sheath width.*—Average 2.6 cm.

*Margin.*—Entire.

*Aspect.*—Mostly flat and folded upward from the midrib.

*Texture, upper and lower surfaces.*—Smooth, glossy, slightly furrowed.

*Venation.*—Parallel.

*Color (upper surface).*—Near RHS green N137A.

*Color (lower surface).*—Near RHS green 144A.

Flower description:

*Inflorescence type.*—Raceme.

*Flower type.*—Single zygomorphic flowers arranged in racemes, flowers roughly pentagonal in shape.

*Flower arrangement.*—Compound alternate.

*Flowering stems.*—Smooth moderately glossy.

*Flowering habit.*—Plants freely flowering; plants typically produce single or double flowering stem(s) with at least 7 to 12 flowers per inflorescence.

*Fragrance.*—Unscented.

*Natural flowering season.*—From February to June in south of Taiwan.

*Post-production longevity.*—Plants of 'TJ Purple Queen' maintain good leaf and flower substance for about 2 to 3 months on the plant under interior environmental conditions.

*Inflorescence length.*—About 30 to 40 cm.

*Inflorescence diameter.*—About 15 to 16 cm.

*Flower diameter.*—About 9.5 to 11.5 cm.

*Flower depth.*—About 4 cm.

Flower bud:

*Flower bud shape.*—Bud apex is orbicular, bud base is ovate.

*Flower bud length.*—About 3 cm.

*Flower bud diameter.*—About 2 cm.

*Flower bud color.*—Yellow-green (RHS145B).

Petals:

*Number of petals.*—2 per flower.

*Length.*—About 6.8 cm.

*Diameter.*—About 6.5 cm.

*Shape.*—Reniform.

*Apex.*—Rounded.

*Base.*—Broad attenuated.

*Margin.*—Entire.

*Texture, upper and lower surfaces.*—Upper surface dull somewhat velvety, lower surface velvety.

*Arrangement of the petals.*—Free.

*Petal main color.*—White (RHS N999D).

*Petal pattern color.*—Light mauve (RHS N81B).

*Petal spot size.*—Medium.

*Petal spot location.*—Toward the base.

Labellum:

*Length.*—About 2.9 cm.

*Diameter.*—About 2.3 cm.

*Shape.*—The labellum is three-lobed with two prominent callosities at the central junction of the lateral lobes and lobes and base of the midlobe.

*Base color of the apical lobe.*—Brilliant orangish yellow (RHS 21B) and purplish red (RHS 71A).

*Shape of the apical lobe.*—Rhombic.

*Average size of the apical lobe.*—About 2.2 cm.

*Color of the labellum whisker.*—White (RHS N999D).

*Average length.*—About 1 cm.

*Shape of the lateral lobe.*—Type IV (UPOV International Union for the Protection of New Varieties of Plants *Phalaenopsis* Guidelines for the Conduct of Tests for Distinctness, Uniformity and Stability 2013).

*Average size of the lateral lobe.*—About 4.5 cm.

*Curvature of the lateral lobe.*—Weak.

*Shape of the callosities.*—Type I (UPOV International Union for the Protection of New Varieties of Plants *Phalaenopsis* Guidelines for the Conduct of Tests for Distinctness, Uniformity and Stability 2013).

*Color of the callosities*.—Purplish red (RHS 71A).
*Average size of the callosities*.—About 0.6 cm.

Sepals:
*Quantity*.—3 per flower.
*Dorsal sepal length*.—About 4.5 cm.
*Lateral sepal length*.—About 4.5 cm.
*Dorsal sepal diameter*.—About 3.4 cm.
*Lateral sepal diameter*.—About 3 cm.
*Shape*.—Ovate to broad elliptic.
*Apex*.—Obtuse to broad bluntly acute.
*Base*.—Broad cuneate.
*Margin*.—Entire.
*Texture, upper and lower surfaces*.—Smooth, dull, somewhat velvety.
*Dorsal sepal main color*.—White (RHS N999D).
*Dorsal sepal pattern color*.—Dark pink violet (RHS N81B).
*Color of the streaks of the dorsal sepal*.—Dark pink violet (RHS N81B).
*Lateral sepal main color*.—White (RHS N999D).
*Lateral sepal pattern color*.—Dark pink violet (RHS N81B).
*Color of the streaks of the lateral sepal*.—Dark pink violet (RHS N81B).

Peduncles:
*Length*.—About 78 to 82 cm.
*Diameter*.—About 0.8 mm.
*Aspect*.—40° angle to rosette.
*Strength*.—Strong.
*Texture*.—Smooth, not very glossy.
*Color*.—In between RHS 137A and RHS199A.

Pedicels:
*Length*.—About 4 cm.
*Diameter*.—About 0.4 mm.
*Aspect*.—About 70° from vertical.
*Strength*.—Moderately strong.
*Texture*.—Smooth moderately glossy.
*Color*.—Yellow (RHS 2D).
*Color towards the base*.—Green (RHS 141D).

Reproductive organs:
*Column*.—Length. — About 1 cm. Diameter. — About 6 mm. Color. — White (RHS N999D). Color towards to apex. — White (RHS N999D).
*Pollinia*.—Quantity of pollen masses. — 2. Diameter. — About 1.8 mm. Color. — Yellow-orange (RHS 22A).
*Ovary*.—Length. — About 5 mm. Diameter. — About 2.5 mm. Color. — White (RHS N999D).
*Root*.—It takes 10 to 20 days for plants growing in tissue culture to initiate roots.

Disease/pest resistance: Strong disease resistance, but no specific resistance or susceptibility to pests has been observed.

Temperature tolerance: The plant can be tolerant to temperature from 16~36° C. The flower can be tolerant from 20~28° C.

What is claimed is:

1. A new and distinct cultivar of *Phalaenopsis* hybrid orchid plant named 'TJ Purple Queen' as illustrated and described.

* * * * *